(12) United States Patent
Schaab et al.

(10) Patent No.: US 11,072,631 B2
(45) Date of Patent: Jul. 27, 2021

(54) METHODS AND INTERMEDIATES FOR THE PREPARATION BILE ACID DERIVATIVES

(71) Applicant: Intercept Pharmaceuticals, Inc., New York, NY (US)

(72) Inventors: Kevin Schaab, Spring Valley, CA (US); Paul E. Whitley, Florence, SC (US); Flavio Chavez Lopez, Florence, SC (US); Kayla R. Iorga, Dalzell, SC (US)

(73) Assignee: Intercept Pharmaceuticals, Inc., New York, NY (US)

( * ) Notice: Subject to any disclaimer, the term of this patent is extended or adjusted under 35 U.S.C. 154(b) by 558 days.

(21) Appl. No.: 15/762,781

(22) PCT Filed: Sep. 23, 2016

(86) PCT No.: PCT/US2016/053483
§ 371 (c)(1),
(2) Date: Mar. 23, 2018

(87) PCT Pub. No.: WO2017/053826
PCT Pub. Date: Mar. 30, 2017

(65) Prior Publication Data

US 2020/0239515 A1 Jul. 30, 2020

Related U.S. Application Data

(60) Provisional application No. 62/222,943, filed on Sep. 24, 2015.

(51) Int. Cl.
*C07J 31/00* (2006.01)
*C07J 9/00* (2006.01)

(52) U.S. Cl.
CPC .............. *C07J 31/006* (2013.01); *C07J 9/00* (2013.01)

(58) Field of Classification Search
CPC . C07J 31/006; C07J 9/00; C07J 9/005; A61K 31/575; A61P 13/12; A61P 1/16; A61P 3/00; A61P 43/00; A61P 9/10
See application file for complete search history.

(56) References Cited

U.S. PATENT DOCUMENTS 5,216,015 A 6/1993 McGarry et al.
7,786,102 B2 8/2010 Pellicciari
(Continued)

FOREIGN PATENT DOCUMENTS

WO WO 2008/002573 A2 1/2008
WO WO 2013/192097 A1 12/2013
(Continued)

OTHER PUBLICATIONS

Diaion 1, Manual of Ion Exchange Resins and Synthetic Absorbents, 1961, Mitsubishi Chemical Corporation, p. i-126. (Year: 1961).*
(Continued)

*Primary Examiner* — Yevgeny Valenrod
*Assistant Examiner* — Blaine G Doletski
(74) *Attorney, Agent, or Firm* — Cooley LLP; Ivor R. Elrifi; Chen Chen

(57) ABSTRACT

The present invention relates to methods and novel intermediates useful in the preparation of a compound of formula (A)

(A)

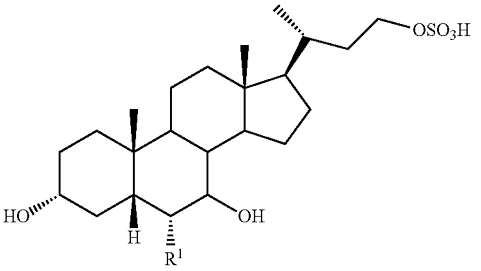

or a pharmaceutically acceptable salt thereof, comprising converting the aldehyde of a compound of formula (B) with a reducing agent to prepare a compound of formula (C)

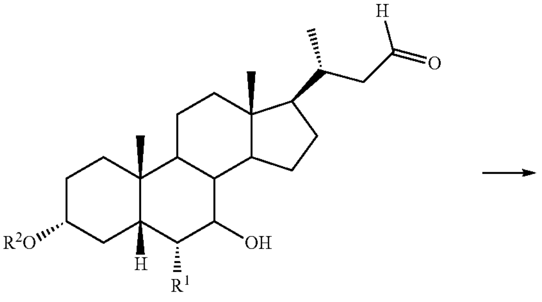

(B)

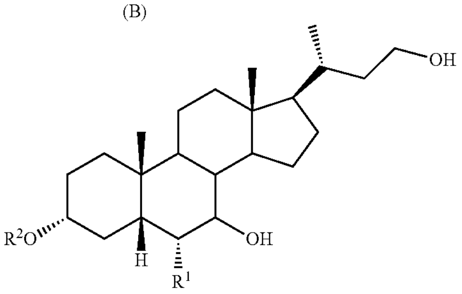

, (C)

and converting the compound of formula (C) with a sulfating reagent to prepare a compound of formula (A). An objective of the present invention is to provide methods of
(Continued)

preparing bile acid derivatives and novel intermediates. A use of the methods and intermediates described relates to the synthesis of bile acid derivatives which activate both FXR and TGR5.

14 Claims, No Drawings

(56) References Cited

U.S. PATENT DOCUMENTS

| | | | | |
|---|---|---|---|---|
| 7,994,352 | B2 | 8/2011 | Ferrari et al. | |
| 8,114,862 | B2 * | 2/2012 | Pellicciari | A61P 9/04 514/182 |
| 2008/0182832 | A1 | 7/2008 | Pellicciari et al. | |
| 2014/0148428 | A1 | 5/2014 | Pruzanski et al. | |
| 2014/0187633 | A1 | 7/2014 | Manku et al. | |

FOREIGN PATENT DOCUMENTS

| | | | | |
|---|---|---|---|---|
| WO | WO 2014/066819 A1 | | 5/2014 | |
| WO | WO-2014066819 A1 | * | 5/2014 | C07J 9/005 |
| WO | WO 2014/085474 A1 | | 6/2014 | |
| WO | WO 2015/181275 A1 | | 12/2015 | |
| WO | WO 2016/127019 A2 | | 8/2016 | |
| WO | WO 2017/027396 A1 | | 2/2017 | |
| WO | WO 2017/053428 A1 | | 3/2017 | |

OTHER PUBLICATIONS

Rizzo G. et al. "Functional Characterization of the Semisynthetic Bile Acid Derivative INT-767, a Dual Farnesoid X Receptor and TGR5 Agonist ", Molecular Pharmacology, 2010, vol. 78, No. 4, p. 617-630.

Thomas C. et al. "Targeting bile-acid signaling for metabolic diseases", Nature Reviews| Drug Discovery, 2008, vol. 7, p. 678-693.

D'Amore C. et al. "Design, Synthesis, and Biological Evaluation of Potent Dual Agonists of Nuclear and Membrane Bile Acid Receptors", Journal of Medicinal Chemistry, vol. 57, No. 3, 2014, pp. 937-954.

Pellicciari et al., "Bile Acid Derivatives as Ligands of the Farnesoid X Receptor. Synthesis, Evaluation, and Structure-Activity Relationship of a Series of Body and Side Chain Modified Analogues of Chenodeoxycholic Acid," J. Med. Chem. (2004) 47:4559-4569.

* cited by examiner

METHODS AND INTERMEDIATES FOR THE PREPARATION BILE ACID DERIVATIVES

BACKGROUND

Bile acids (BAs) are well known for their role in the solubilization and digestion of lipid-soluble nutrients. Recently, BAs have emerged as signaling molecules with systemic endocrine functions. BAs and derivatives thereof have been shown to modulate several nuclear hormone receptors, notably the farnesoid X receptor (FXR), and are agonists for the G protein-coupled receptor TGR5. Signaling via FXR and TGR5 modulates several metabolic pathways, regulating not only BA synthesis and enterohepatic recirculation, but also triglyceride, cholesterol, glucose and energy homeostasis (Thomas, et al. Nat Rev Drug Discovery, 2008, 7, 678-693).

6α-Ethyl-3α,7α,23-trihydroxy-24-nor-5β-cholan-23-sulfate sodium salt (herein referred to as "INT-767") is a dual agonist targeting both FXR and TGR5.

INT-767

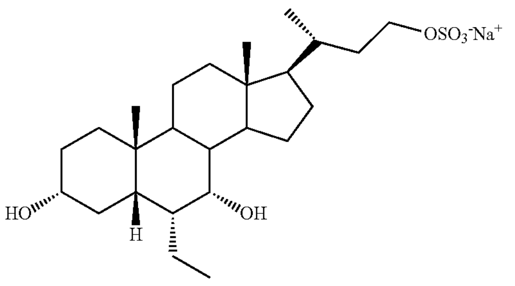

INT-767 induces FXR-dependent lipid uptake by adipocytes and increases TGR5-dependent secretion of GLP-1 by enteroendocrine cells. In-vivo efficacy of INT-767 treatment is demonstrated by decreased cholesterol and triglyceride levels in diabetic db/db mice and in mice rendered diabetic by streptozotocin administration (Adorini, et al. Molecular Pharmacology, 2010, 78, 617-630). A dual agonist targeting both FXR and TGR5 could be useful not only in treating a variety of liver and metabolic diseases, but also kidney and gastrointestinal disorders.

Various methods of synthesizing INT-767 have been described, for example, in WO2008/002573, and more recently WO2014/066819. However, there remain needs for methods that are capable of preparing INT-767 with a reduced number of steps, an increased yield, and higher purity. The present application addresses these needs.

SUMMARY OF THE INVENTION

An objective of the present invention is to provide methods of preparing bile acid derivatives and novel intermediates. A use of the methods and intermediates described herein relates to the synthesis of bile acid derivatives which activate both FXR and TGR5.

In one aspect, the present invention relates to a method of preparing a compound of formula (A):

(A)

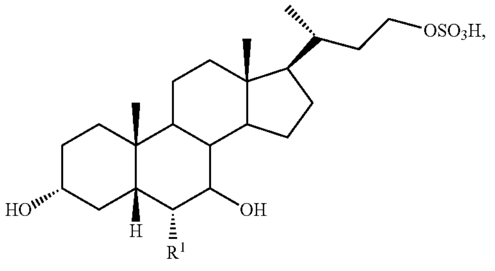

or a pharmaceutically acceptable salt thereof, wherein $R^1$ is H or $C_1$-$C_6$ alkyl; the method comprising the steps of:

(a) converting the aldehyde of a compound of formula (B) with a reducing agent to prepare a compound of formula (C)

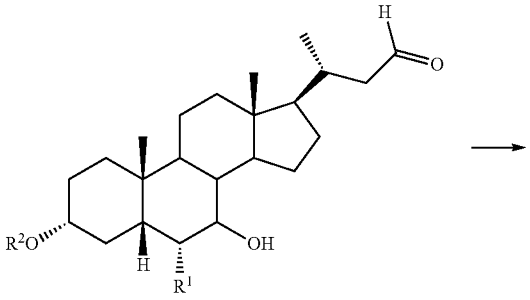

(B)

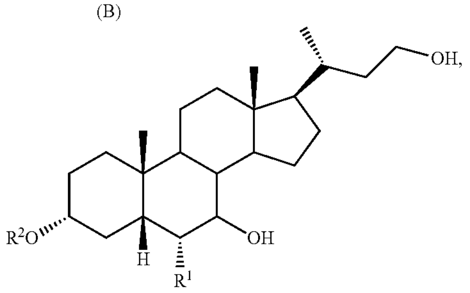

(C)

wherein $R^2$ is a protecting group;

(b) converting the compound of formula (C) with a sulfating reagent to prepare a compound of formula (D)

(D)

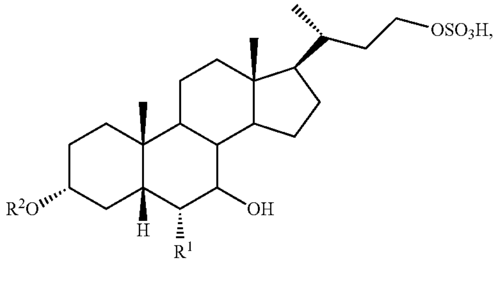

or a pharmaceutically acceptable salt thereof; and (c) deprotecting the C-3 hydroxyl of the compound of formula (D).

Another objective of the present invention is to provide novel compounds which are used as intermediates in the methods described herein.

In one aspect, the intermediate is a compound of formula (B):

(B)

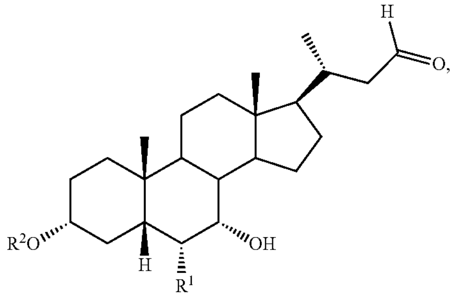

wherein $R^1$ is H or $C_1$-$C_6$ alkyl; and $R^2$ is a protecting group.

Another objective of the present invention is to provide a method of preparing the sodium salt of a compound of formula (A):

(A)

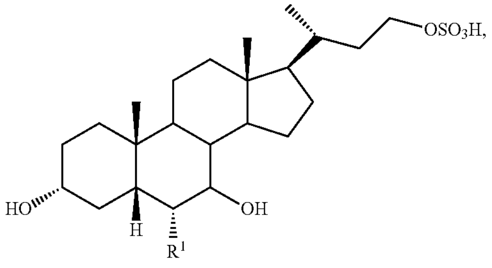

wherein $R^1$ is H or $C_1$-$C_6$ alkyl, the method comprising the steps of:

(a) dissolving a compound of formula (A) or a pharmaceutically acceptable salt thereof in an aqueous solution; and (b) passing the aqueous solution through a cation-exchange resin.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. The materials, methods, and examples are illustrative only and are not intended to be limiting.

Other features and advantages of the invention will be apparent from the following detailed description.

DETAILED DESCRIPTION

Definitions

Certain terms used in the specification and claims are collected here.

The term "$C_1$-$C_6$ alkyl", as used herein, refers to a straight-chain or branched hydrocarbon moiety having 1, 2, 3, 4, 5, or 6 carbon atoms. Examples of $C_1$-$C_6$ alkyl moieties include, but are not limited to, methyl, ethyl, n-propyl, isopropyl, cyclopropyl, n-butyl, isobutyl, sec-butyl, t-butyl, n-pentyl, isopentyl, and n-hexyl. "$C_1$-$C_4$ alkyl" refers to a straight-chain or branched hydrocarbon moiety having 1, 2, 3, or 4 carbon atoms.

The term "DCM", as used herein, refers to dichloromethane.

As used herein, the term "MTBE" refers to methyl tert-butyl ether.

The term "THF", as used herein, refers to tetrahydrofuran.

As used herein, the term "EtOAc" refers to ethyl acetate.

The term "Hex", as used herein, refers to hexanes.

As used herein, the term "WFI" refers to water for injection.

As used herein, the term "TLC" refers to thin layer chromatography.

As used herein, the term "HPLC" refers to high performance liquid chromatography.

The term "Pyr", as used herein, refers to pyridine.

As used herein, the term "reducing reagent" refers to a reagent that converts, for example, an aldehyde to an alcohol.

The term "sulfating reagent" refers to a reagent that converts, for example, an alcohol to a sulfate.

As used herein, the term "protecting group" refers to an appropriate moiety for masking, for example, a hydroxyl functionality which is stable/non-reactive under the reaction condition (e.g., non-reactive with an agent used in the reaction). One skilled in the art will recognize the particular moieties employed for protecting a hydroxyl group instead of another functionality, e.g. carboxylic acid.

The term "cation exchange" refers to a process by which a cation in a liquid phase exchanges with another cation present as the counter ion of a negatively charged solid polymer. Cation exchange may be used chromatographically, to separate cations.

As used herein, the term "cation exchange resin", refers to polymers that are capable of exchanging particular ions within the polymer with cations in a solution that is passed through them. The cation exchange resin has a higher affinity for the cation in solution compared to the cation in the resin. Cation exchange resins may be based on polystyrene sulfonates.

As used herein, the term "pharmaceutically acceptable salt" refers to base addition salts including, but are not limited to, alkali metal salts selected from sodium, lithium or potassium salt or alkaline earth metal salts selected from calcium or magnesium. Base addition salts further include inorganic and organic amine salts including, but are not limited to, ammonium, methylammonium, ethylammonium, diethylammonium, triethylammonium, lysine, arginine, N-methylglucamine and choline.

The phrase "pharmaceutically acceptable carrier" is art-recognized, and includes, for example, pharmaceutically acceptable materials, compositions or vehicles, such as a liquid or solid filler, diluent, excipient, solvent or encapsulating material, involved in carrying or transporting any subject composition from one organ, or portion of the body, to another organ, or portion of the body.

As used herein, the term "pharmaceutically acceptable excipient" refers to an excipient that is useful in preparing a pharmaceutical composition that is generally safe, non-toxic and neither biologically nor otherwise undesirable, and includes excipient that is acceptable for veterinary use as well as human pharmaceutical use.

"Solvate", as used herein, refers to a solvent addition form of a compound of formula (A) that contains either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

A "pharmaceutical composition" is a formulation containing a compound of formula (A) or a pharmaceutically acceptable salt thereof. In one embodiment, the pharmaceutical composition is in bulk or in unit dosage form. The unit dosage form is any of a variety of forms, including, for example, a capsule, an IV bag, a tablet, a single pump on an aerosol inhaler, or a vial. The quantity of active ingredient (e.g., a formulation of a compound of the invention or salts thereof) in a unit dose of composition is an effective amount and is varied according to the particular treatment involved. One skilled in the art will appreciate that it may be necessary to make routine variations to the dosage depending, for example, on the age and condition of the patient. The dosage will also depend on the route of administration. A variety of routes are contemplated, including oral, ocular, ophthalmic, pulmonary, rectal, parenteral, transdermal, subcutaneous, intravenous, intramuscular, intraperitoneal, intranasal, and the like. Dosage forms for the topical or transdermal administration of a compound of this application include powders, sprays, ointments, pastes, creams, lotions, gels, solutions, patches and inhalants. In another embodiment, the active compound is mixed under sterile conditions with a pharmaceutically acceptable carrier, and with any preservatives, buffers, or propellants that are required.

As defined herein, the term "metabolite" refers to glucuronidated and sulfated derivatives of the compounds of formula (A), wherein one or more glucuronic acid or sulphate moieties are linked to the compound. Glucuronic acid moieties may be linked to the compounds through glycosidic bonds with the hydroxyl groups of the compounds (e.g., 3-hydroxyl and/or 7-hydroxyl). Sulphated derivatives of the compounds may be formed through sulfation of the hydroxyl groups (i.e., 3-hydroxyl or 7-hydroxyl). Examples of metabolites include, but are not limited to, 3-O-glucuronide, 7-O-glucuronide, and 3-O-7-O-glucuronide, of the compounds of formula (A), and 3-sulphate, 7-sulphate, and 3,7-bisulphate derivatives, of the compounds of formula (A).

The term "treating", as used herein, refers to relieving, lessening, reducing, eliminating, modulating, or ameliorating, i.e., causing regression of the disease state or condition.

The term "preventing", as used herein, refers to completely or almost completely stop a disease state or condition, from occurring in a patient or subject, especially when the patient or subject is predisposed to such or at risk of contracting a disease state or condition. Preventing can also include inhibiting, i.e., arresting the development, of a disease state or condition, and relieving or ameliorating, i.e., causing regression of the disease state or condition, for example when the disease state or condition may already be present.

The phrase "reducing the risk of", as used herein, refers to lowering the likelihood or probability of a central nervous system disease, inflammatory disease and/or metabolic disease from occurring in a patient, especially when the subject is predisposed to such occurrence.

As used herein, the term "about" or "approximately", or the like, when used together with a numeric value, may include a range of numeric values which is more or less than the numeric value to which the term refers or relate. For example, the range can include numeric values that are from 5% less to 5% more, from 4% less to 4% more, from 3% less to 3% more, from 2% less to 2% more, or from 1% less to 1% more, than the numeric value to which the term refers or relate. For example, "about 5" can include numeric values from 4.5 to 5.5, from 4.55 to 5.45, from 4.6 to 5.4, from 4.65 to 5.35, from 4.7 to 5.3, from 4.75 to 5.25, from 4.8 to 5.2, from 4.85 to 5.15, from 4.9 to 5.1, or from 4.95 to 5.05.

Methods of the Invention

In one aspect, the present invention relates to a method of preparing a compound of formula (A):

(A)

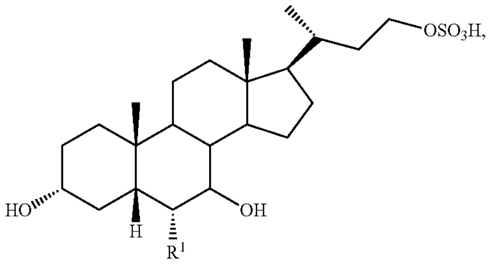

or a pharmaceutically acceptable salt thereof, wherein $R^1$ is H or $C_1$-$C_6$ alkyl; the method comprising the steps of:

(a) converting the aldehyde of a compound of formula (B) with a reducing reagent to prepare a compound of formula (C)

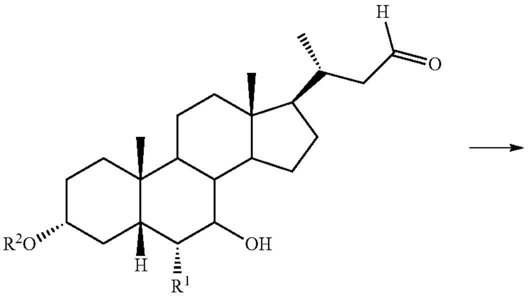

(B)

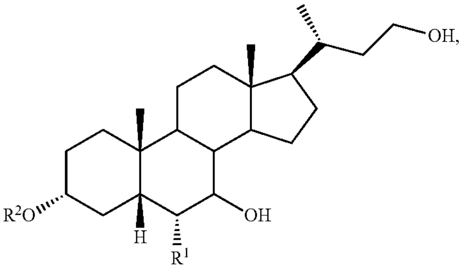

(C)

wherein $R^2$ is a protecting group;

(b) converting of the compound of formula (C) with a sulfating reagent to prepare a compound of formula (D)

(D)

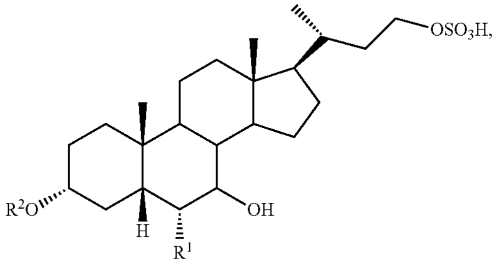

or a pharmaceutically acceptable salt thereof; and (c) deprotecting the C-3 hydroxyl of the compound of formula (D).

In one embodiment, the compound prepared by the method of the present invention is a compound of formula (A), wherein $R^1$ is $C_1$-$C_4$ alkyl. In another embodiment, $R^1$ is methyl, ethyl or propyl. In yet another embodiment, $R^1$ is ethyl.

In one embodiment, the compound prepared by the method of the present invention is a compound of formula (A), wherein the C-7 hydroxyl is in the alpha-orientation. In one embodiment, C-7 hydroxyl is in the beta-orientation.

In yet another embodiment, the compound prepared by the method of the present invention is a compound of formula (A), wherein $R^1$ is $C_1$-$C_4$ alkyl and C-7 hydroxyl is in the alpha-orientation. In one embodiment, $R^1$ is ethyl and C-7 hydroxyl is in the alpha-orientation.

In one embodiment, the compound prepared by the method of the present invention is a compound of formula (A) wherein the $R^2$ protecting group is selected from C(O) $C_1$-$C_4$ alkyl, $C_1$-$C_6$ alkoxycarbonyl, optionally substituted aryloxycarbonyl, benzoyl, benzyl, pivaloyl, tetrahydropyranyl ether, tetrahydrofuranyl, 2-methoxyethoxymethyl ether, methoxymethyl ether, ethoxyethyl ether, p-methoxybenzyl ether, methylthiomethyl ether, triphenylmethyl, dimethoxytrityl, methoxytrityl, and silyl ether. In one embodiment, the silyl ether is selected from trimethylsilyl ether, triethylsilyl ether, triisopropylsilyl ether, tert-butyldimethylsilyl ether, and tert-butyldiphenylsilyl ether. In one embodiment, the $R^2$ protecting group is benzoyl or acetyl. In one embodiment, the $R^2$ protecting group is $C(O)C_1$-$C_4$ alkyl. In one embodiment, the $R^2$ protecting group is acetyl.

In one embodiment, the reducing reagent in step (a) is $NaBH_4$, $NaCNBH_3$, $LiBH_4$, $(i\text{-}Bu_2AlH)_2$, or an organoborane. In one embodiment, the reducing reagent is $NaBH_4$. In one embodiment, the molar ratio of the reducing reagent is from about 3 equivalents to about 2 equivalents. In another embodiment, the molar ratio is about 2.2 equivalents.

The reduction in step (a) is performed by using a suitable solvent. In one embodiment, the reduction is performed in an alcoholic solvent. In one embodiment, the alcoholic solvent is methanol. In one embodiment, the alcoholic solvent is isopropanol. In one embodiment, the alcoholic solvent is ethanol.

In one embodiment, the reduction in step (a) is conducted in a time period between about 2 hours and about 48 hours, e.g., 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, as well as any time increment in between.

In one embodiment, the reduction in step (a) is performed at a temperature from between about −10° C. and about 15° C., e.g., −10° C., −5° C., 0° C., 3° C., 5° C., 7° C. and 10° C., as well as any temperature increment in between. In one embodiment, the reduction is performed at about 5° C.

In another embodiment, the sulfating reagent in step (b) is selected from sulfur trioxide pyridine, sulfur trioxide trimethylamine, sulfur trioxide triethylamine, sulfur trioxide N,N-dimethylformamide, sulfur trioxide pyridine polymer bound (i.e. poly(4-vinylpyridine) sulfur trioxide), chlorosulfonic acid, oleum, or sulfamic acid. In one embodiment, the sulfating reagent is sulfur trioxide trimethylamine. In one embodiment, the sulfating reagent is sulfur trioxide triethylamine. In one embodiment, the sulfating reagent is sulfur trioxide N,N-dimethylformamide. In one embodiment, the sulfating reagent is sulfur pyridine complex polymer bound (i.e. poly(4-vinylpyridine) sulfur trioxide). In one embodiment, the sulfating reagent is oleum. In one embodiment, the sulfating reagent is sulfur trioxide pyridine. In embodiment, the molar ratio of the sulfating reagent is between about 1.3 equivalents and about 1.0 equivalent. In another embodiment, the molar ratio is about 1.05 equivalents.

In one embodiment, the conversion in step (b) is conducted in a time period between about 30 minutes and about 3 hours, e.g., 30 minutes, 45 minutes, 1 hour, 1.5 hours, 2 hours, 3 hours, as well as any time increment in between.

In one embodiment, the deprotection in step (c) is performed under acidic conditions using hydrochloric acid. In one embodiment, the deprotection is performed with amberlyst $H^+$ resin. In one embodiment, the ratio of the amberlyst $H^+$ resin is between about 1.0 wt./wt. % and about 0.3 wt./wt. % with respect to the amount of the compound of formula (D). In another embodiment, the ratio is about 0.5 wt./wt. %.

In one embodiment, the compound prepared by the method of the present invention is compound 7B:

(7B)

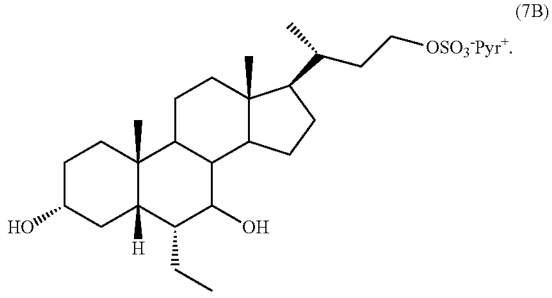

In one embodiment, the method further comprises converting compound 7B to compound 7C:

(7C)

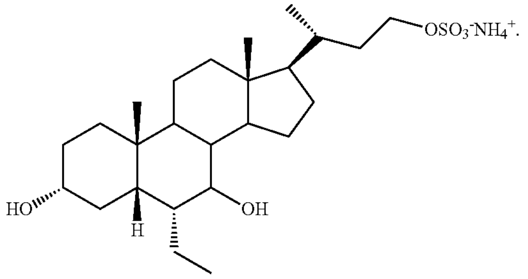

In one embodiment, the conversion to compound 7C is prepared by dissolving compound 7B in a basic aqueous solution containing ammonium. In one embodiment, the basic solution is aqueous ammonium hydroxide. In one embodiment, the basic solution is about 28% aqueous ammonium hydroxide. In one embodiment, the aqueous ammonium hydroxide maintains a pH of >8 during the conversion.

In one embodiment, the method further comprises converting compound 7C to compound 7:

(7)

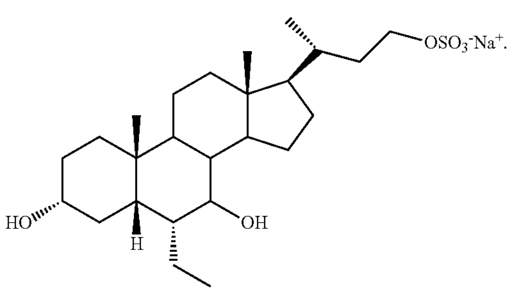

In one embodiment, the conversion to Compound 7 comprises the steps of:

(a) dissolving Compound 7C in an aqueous solution; and (b) passing the aqueous solution through a cation-exchange resin.

In another aspect, the method further comprises converting a compound of formula (E) to prepare the compound of formula (B):

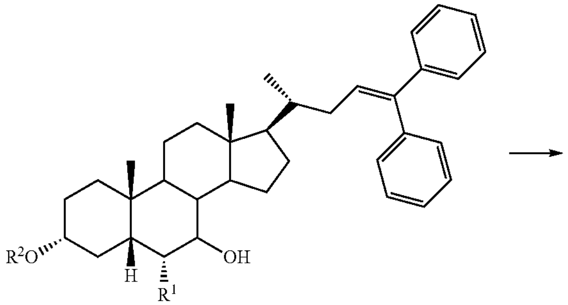

(E)

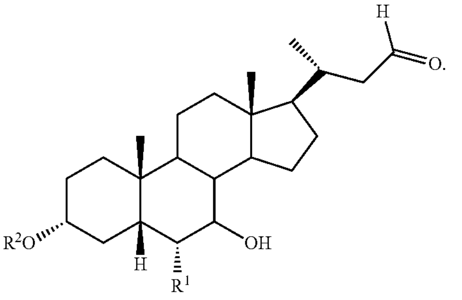

(B)

In one embodiment, the compound of formula (E) is treated with ozone followed by the addition of triphenylphosphine or dimethyl sulfide. In another embodiment, the ozone contains oxygen. In one embodiment, dimethyl sulfide is used. In another embodiment, triphenylphosphine is used. In one embodiment, the molar ratio of triphenylphosphine or dimethyl sulfide is between about 1.3 equivalents and about 1 equivalent. In another embodiment, the molar ratio is about 1.12 equivalents. In one embodiment, the conversion is performed in an alcoholic solvent. In one embodiment, the alcoholic solvent is methanol. In one embodiment, the conversion is performed at a temperature between about −70° C. and about −50° C., e.g., −70° C., −65° C., −60° C., −55° C., and −50° C., as well as any temperature increment in between.

In another aspect, the method further comprises protecting the C-3 hydroxyl of a compound of formula (F) to prepare the compound of formula (E):

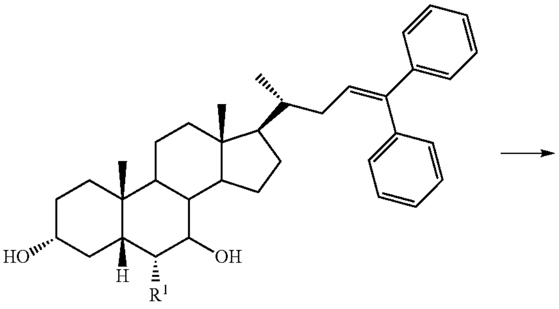

(F)

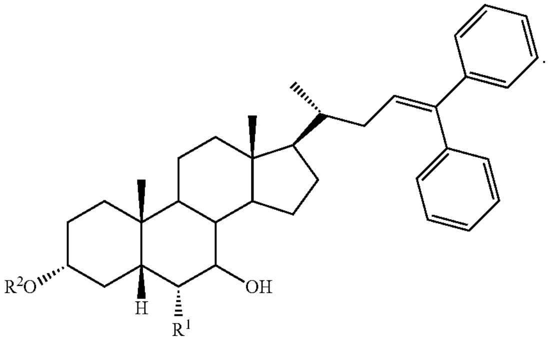

(E)

In one embodiment, the compound of formula (F) is treated with acetic anhydride. In one embodiment, the molar ratio of acetic anhydride is between about 2.0 equivalents and about 1 equivalent. In another embodiment, the molar ratio is about 1.66 equivalents. In one embodiment, the conversion is catalyzed by dimethylaminopyridine. In another embodiment, pyridine is used in the conversion. In another embodiment, the conversion is performed in diethyl ether or tetrahydrofuran. In one embodiment, the conversion is performed at a temperature below 30° C.

In one aspect, the method further comprises converting a compound of formula (G) to prepare the compound of formula (F):

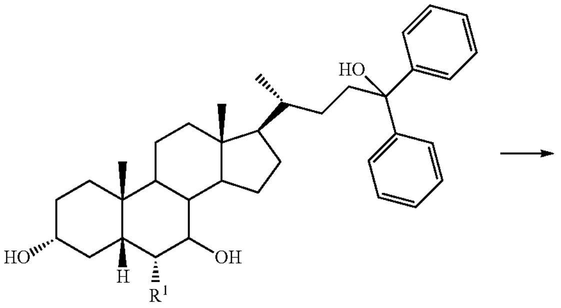

(G)

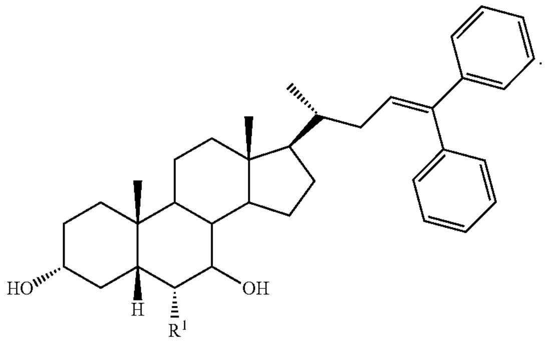

(F)

In one embodiment, the compound of formula (G) is treated with p-toluenesulfonic acid. In one embodiment, the molar ratio of p-toluenesulfonic acid is from about 0.1 equivalents to about 0.02 equivalents. In another embodiment, the molar ratio is about 0.05 equivalents. In one embodiment, the conversion is performed in an alcoholic solvent. In one embodiment, the alcoholic solvent is ethanol. In one embodiment, the conversion to is performed at a temperature between about 50° C. and about 90° C., e.g., 50° C., 60° C., 70° C., 75° C., 80° C., and 90° C., as well as any temperature increment in between.

In another aspect, the method further comprises converting a compound of formula (H) to prepare the compound of formula (G):

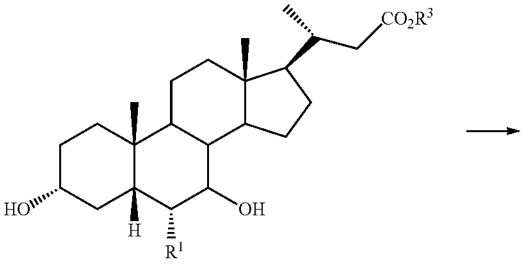

(H)

-continued

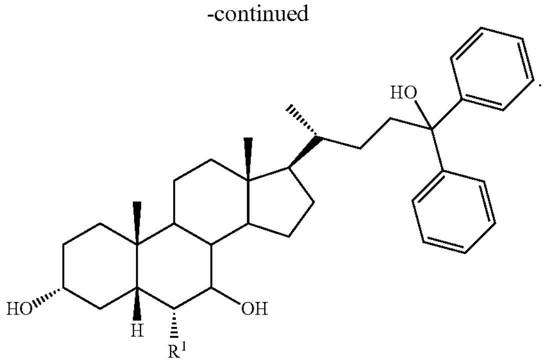

(G)

In one embodiment, the compound of formula (H) is treated with phenylmagnesium bromide. In another embodiment, the molar ratio of phenylmagnesium bromide is about 2 equivalents to about 6 equivalents. In another embodiment, the molar ratio is about 5 equivalents. In one embodiment, the conversion is performed in a non-protic solvent. In one embodiment, the non-protic is tetrahydrofuran. In one embodiment, the conversion is performed at a temperature between about 25° C. and about 70° C., e.g., 25° C., 30° C., 40° C., 50° C., 60° C., and 70° C., as well as any temperature increment in between.

In one aspect, the method further comprises converting a compound of formula (I) to afford the compound of formula (H):

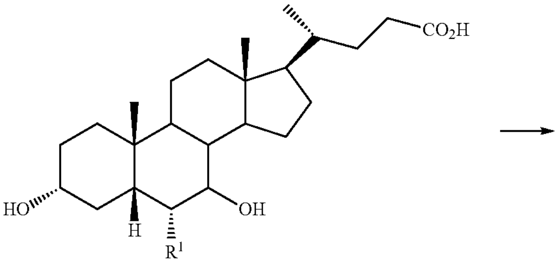

(I)

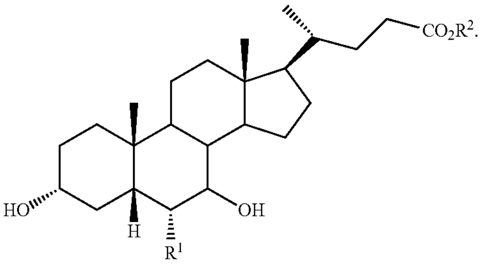

(H)

In one embodiment, the compound of formula (I) is esterified with a $C_1$-$C_6$ alcohol. In one embodiment, the $C_1$-$C_6$ alcohol is methanol or ethanol. In one embodiment, the $C_1$-$C_6$ alcohol is methanol. In another embodiment, the conversion is catalyzed with an acid. In another embodiment, the acid is delivered by $H^+$ Dowex resin. In one embodiment, the conversion is performed at a temperature between about 55° C. and about 85° C., e.g., 55° C., 65° C., 75° C., and 85° C., as well as any temperature increment in between.

Another objective of the present invention is to provide novel compounds which are used as intermediates in the methods described herein. In one aspect, the intermediate is a compound of formula (B):

(B)

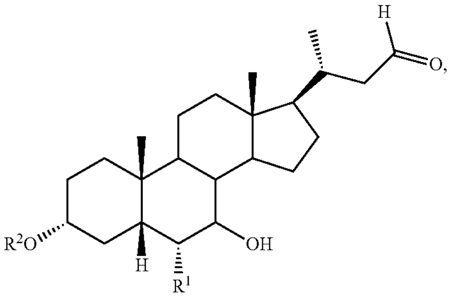

wherein $R^1$ is H or $C_1$-$C_6$ alkyl; and $R^2$ is a protecting group.

In one embodiment, the intermediate is a compound of formula (B) wherein $R^1$ is $C_1$-$C_4$ alkyl. In another embodiment, $R^1$ is methyl, ethyl or propyl. In yet another embodiment, $R^1$ is ethyl. In one embodiment, the C-7 hydroxyl is in the alpha-orientation. In one embodiment, C-7 hydroxyl is in the beta-orientation. In one embodiment, the $R^2$ protecting group is selected from $C(O)C_1$-$C_4$ alkyl, $C_1$-$C_6$ alkoxycarbonyl, optionally substituted aryloxycarbonyl, benzoyl, benzyl, pivaloyl, tetrahydropyranyl ether, tetrahydrofuranyl, 2-methoxyethoxymethyl ether, methoxymethyl ether, ethoxyethyl ether, p-methoxybenzyl ether, methylthiomethyl ether, triphenylmethyl, dimethoxytrityl, methoxytrityl, and silyl ether. In one embodiment, the silyl ether is selected from trimethylsilyl ether, triethylsilyl ether, triisopropylsilyl ether, tert-butyldimethylsilyl ether, and tert-butyldiphenylsilyl ether. In one embodiment, the $R^2$ protecting group is benzoyl or acetyl. In one embodiment, the $R^2$ protecting group is $C(O)C_1$-$C_4$ alkyl. In one embodiment, the $R^2$ protecting group is acetyl.

In one embodiment, the compound of formula (B) is:

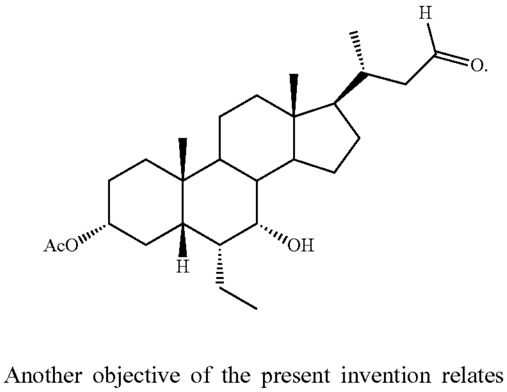

Another objective of the present invention relates to a method of preparing the sodium salt of a compound of formula (A)

(A)

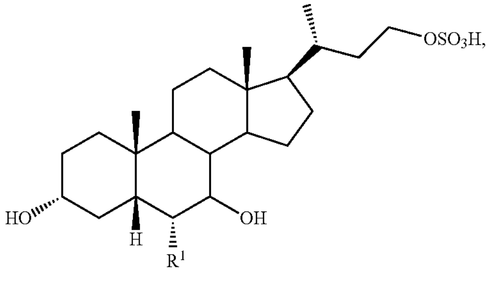

wherein $R^1$ is H or $C_1$-$C_6$ alkyl, the method comprising the steps of:

(a) dissolving a compound of formula (A) or a pharmaceutically acceptable salt thereof in an aqueous solution; and (b) passing the aqueous solution through a cation-exchange resin.

In one embodiment, the sodium salt of a compound of formula (A) is prepared from the free base. In one embodiment, the sodium salt of a compound of formula (A) is prepared from the ammonium salt. In one embodiment, the sodium salt of a compound of formula (A) is prepared from the pyridinium salt. In another embodiment, the cation-exchange resin is DIAION™ resin $Na^+$ form. In one embodiment, the aqueous solution in step (a) is washed with a mixture of methyl tert-butyl ether/2-methyl-tetrahydrofuran before passing through the cation-exchange resin. In another embodiment, the aqueous solution passed through the cation-exchange resin is lyophilized. In another embodiment, the lyophilized product is polish filtered to remove sodium sulfate. In one embodiment, the sodium salt of a compound of formula (A) is further purified by reverse phase chromatography.

In one aspect, the method of the present application produces a substantially pure compound of formula (A), or a pharmaceutically acceptable salt thereof. The term "purity" as used herein refers to the amount of compound of formula (A) based on analytic methods commonly used in the art (e.g., HPLC). Purity is based on the "organic" purity of the compound, and does not include a measure of any amount of water, solvent, metal, inorganic salt, etc. In one embodiment, the purity of the compound of formula (A) is compared to the purity of the reference standard by comparing the area under the peak in HPLC. In one embodiment, the compound of formula (A) has a purity of greater than about 96%. In one embodiment, the compound of formula (A) has a purity of greater than about 98%. For example, the purity of the synthesized compound of Formula (A) is 96.0%, 96.1%, 96.2%, 96.3%, 96.4%, 96.5%, 96.6%, 96.7%, 96.8%, 96.9%, 97.0%, 97.1%, 97.2%, 97.3%, 97.4%, 97.5%, 97.6%, 97.7%, 97.8%, 97.9%, 98.0%, 98.1%, 98.2%, 98.3%, 98.4%, 98.5%, 98.6%, 98.7%, 98.8%, 98.9%, 99.0%, 99.1%, 99.2%, 99.3%, 99.4%, 99.5%, 99.6%, 99.7%, 99.8%, or 99.9%. For example, the purity of the synthesized compound of formula (A) is 98.0%, 98.1%, 98.2%, 98.3%, 98.4%, 98.5%, 98.6%, 98.7%, 98.8%, 98.9%, 99.0%, 99.1%, 99.2%, 99.3%, 99.4%, 99.5%, 99.6%, 99.7%, 99.8%, or 99.9%. For example, the purity of the synthesized compound of formula (A) is 98.0%, 98.5%, 99.0%, 99.5%, 99.6%, 99.7%, 99.8%, or 99.9%. For example, the purity of the synthesized compound of formula (A) is 98.5%, 99.0%, or 99.5%. In one embodiment, the purity is determined by HPLC.

The present application provides methods for the synthesis of highly pure compounds of formula (A) which is safe and which produces compounds of formula (A) on a large scale. In one embodiment, the method of the present application produces compounds of formula (A) in high yield and purity (>98%).

Pharmaceutical Compositions

The present application further provides compounds of formula (A) for oral administration. In one embodiment, the formulation is oral administration for the prevention and treatment of FXR and/or TGR5 mediated diseases and conditions.

Formulations suitable for oral administration may be provided as discrete units, such as tablets, capsules, cachets (wafer capsule used by pharmacists for presenting a drug), lozenges, each containing a predetermined amount of one or more compounds of formula (A); as powders or granules; as solutions or suspensions in aqueous or non-aqueous liquids; or as oil-in-water or water-in-oil emulsions.

Formulations of the present application may be prepared by any suitable method, typically by uniformly and intimately admixing one or more compounds of Formula (A) with liquids or finely divided solid carriers or both, in the required proportions and, if necessary, shaping the resulting mixture into the desired shape.

For example, a tablet may be prepared by compressing an intimate mixture comprising a powder or granules of one or more compounds of Formula (A) and one or more optional ingredients, such as a binder, lubricant, inert diluent, or surface active dispersing agent, or by molding an intimate mixture of powdered active ingredient and inert liquid diluent.

For example, one or more tablets may be administered to get to a target dose level based on the subject's weight, e.g., a human between about 50 kg to about 100 kg.

In addition to the ingredients specifically mentioned above, the oral formulations of the present application may include other agents known to those skilled in the art of pharmacy, having regard for the type of formulation in issue. Oral formulations suitable may include flavouring agents.

In one embodiment, the present application relates to a pharmaceutical formulation of one or more compounds of formula (A), or a pharmaceutically acceptable salt, solvate, or amino acid conjugate thereof, wherein one or more compounds of formula (A) is produced by a process of the application. In another embodiment, the formulation is administered orally.

In one embodiment, the formulation is in tablet form. In another embodiment, the formulation comprises one or more compounds of Formula (A) and one or more components selected from microcrystalline cellulose, sodium starch glycolate, magnesium stearate, coating material, or colloidal silicon dioxide. In one embodiment, the coating material is an Opadry® coating material.

All percentages and ratios used herein, unless otherwise indicated, are by weight. The percent dimeric impurity is on an area percent basis, typically as quantified by analytical HPLC.

Methods of Treatment

Compounds of formula (A) and pharmaceutically acceptable salts thereof, are useful for a variety of medicinal purposes. Compounds of formula (A) may be used in methods for the prevention or treatment of FXR and/or TGR5 mediated diseases and conditions. In one embodiment, the disease or condition is selected from biliary atresia, cholestatic liver disease, chronic liver disease, nonalcoholic steatohepatitis (NASH), hepatitis C infection, alcoholic liver disease, primary biliary cirrhosis (PBC), liver damage due to progressive fibrosis, liver fibrosis, and cardiovascular diseases including atherosclerosis, arteriosclerosis, hypercholesteremia, and hyperlipidemia. In one embodiment, the compounds of formula (A) may be used in methods for lowering triglycerides and/or increasing HDL. Other effects of compounds of formula (A) include lowering alkaline phosphatase (ALP), bilirubin, ALT, AST, and GGT. In one embodiment, the present application relates to a pharmaceutical composition comprising one or more compounds of formula (A) and a pharmaceutically acceptable carrier, wherein the one or more compounds of formula (A), or a pharmaceutically acceptable salt, solvate, or amino acid conjugate thereof, is produced by a method of the present application.

In one embodiment, the compound or pharmaceutical composition is administered orally, parenterally, or topically. In one embodiment, the compound or pharmaceutical composition is administered orally.

In one embodiment, the present application relates to a method for inhibiting fibrosis in a subject who is suffering from a cholestatic condition, the method comprising the step of administering to the subject an effective amount of one or more compounds of formula (A) or a pharmaceutical composition thereof, wherein the one or more compounds of formula (A) is produced by the method of the present application. In one embodiment, the present application relates to a method for inhibiting fibrosis in a subject who is not suffering from a cholestatic condition, the method comprising the step of administering to the subject an effective amount of one or more compounds of formula (A) or a pharmaceutical composition thereof, wherein the one or more compounds of formula (A) is produced by the method of the present application. In one embodiment, the fibrosis to be inhibited occurs in an organ where FXR is expressed.

In one embodiment, the cholestatic condition is defined as having abnormally elevated serum levels of alkaline phosphatase, 7-glutamyl transpeptidase (GGT), and 5' nucleotidase. In another embodiment, the cholestatic condition is further defined as presenting with at least one clinical symptom. In another embodiment, the symptom is itching (pruritus). In another embodiment, the fibrosis is selected from the group consisting of liver fibrosis, kidney fibrosis, and intestinal fibrosis. In another embodiment, the cholestatic condition is selected from the group consisting of primary biliary cirrhosis, primary sclerosing cholangitis, drug-induced cholestasis, hereditary cholestasis, and intrahepatic cholestasis of pregnancy. In another embodiment, the subject is not suffering from a cholestatic condition associated with a disease or condition selected from the group consisting of primary liver and biliary cancer, metastatic cancer, sepsis, chronic total parenteral nutrition, cystic fibrosis, and granulomatous liver disease.

In one embodiment, the subject has liver fibrosis associated with a disease selected from the group consisting of hepatitis B; hepatitis C; parasitic liver diseases; post-transplant bacterial, viral and fungal infections; alcoholic liver disease (ALD); non-alcoholic fatty liver disease (NAFLD); non-alcoholic steatohepatitis (NASH); liver diseases induced by methotrexate, isoniazid, oxyphenistatin, methyldopa, chlorpromazine, tolbutamide, or amiodarone; autoimmune hepatitis; sarcoidosis; Wilson's disease; hemochromatosis; Gaucher's disease; types III, IV, VI, IX and X glycogen storage diseases; $\alpha_1$-antitrypsin deficiency; Zellweger syndrome; tyrosinemia; fructosemia; galactosemia; vascular derangement associated with Budd-Chiari syndrome, veno-occlusive disease, or portal vein thrombosis; and congenital hepatic fibrosis.

In one embodiment, the subject has intestinal fibrosis associated with a disease selected from the group consisting of Crohn's disease, ulcerative colitis, post-radiation colitis, and microscopic colitis.

In one embodiment, the subject has renal fibrosis associated with a disease selected from the group consisting of diabetic nephropathy, hypertensive nephrosclerosis, chronic glomerulonephritis, chronic transplant glomerulopathy, chronic interstitial nephritis, and polycystic kidney disease.

EXAMPLES

The following examples are intended to illustrate certain embodiments of the present invention, but do not exemplify the full scope of the invention.

Example 1. Synthesis of a Compound of Formula (I)

(I)

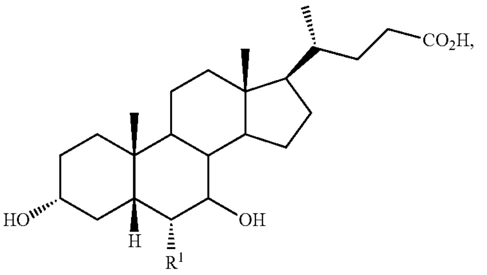

wherein $R^1$ is H or $C_1$-$C_6$ alkyl,

Compounds of formula (I) may be readily prepared by those skilled in the art. In particular, compounds of the invention may be prepared according to the published procedures in U.S. Pat. Nos. 7,786,102 and 7,994,352.

Example 2. Synthesis of Compound 1

(1)

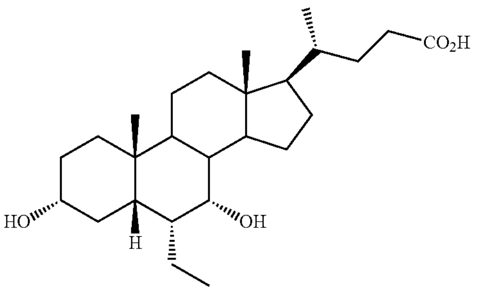

Compound 1 can be prepared according to the published procedure in WO 2013/192097. In this procedure, 3α-hydroxy-7-keto-5β-cholanic acid (KCLA) was used as the commercially available starting material.

Example 3. Synthesis of Compound 7 (INT-767)

(7)

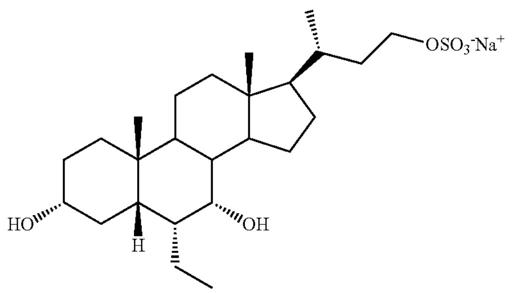

Compound 1 was used as the starting material. Broadly, the side-chain acid of compound 1 was shortened by one carbon. The resulting alcohol was converted to the sulfate and further to the sodium salt. Specifically, esterification of Compound 1, followed by a Grignard reaction (steps 1 and 2, respectively) provided carbinol Compound 3. Following dehydration (step 3) and acetate protection (step 4), the resulting Compound 4 was ozonized (step 5A), reduced (step 5B), and purified by column chromatography (step 5C). Step 6 was separated into 3 stages: step 6A (the sulfonation), step 6B (the deprotection and salt switch), and step 6C (the conversion to $Na^+$ salt, lyophilization, $Na_2SO_4$ removal, and re-lyophilization).

Step 1. Synthesis of Compound 2

(2)

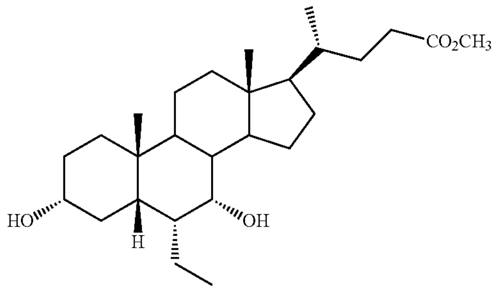

To a reaction vessel, was charged compound 1 (1.064 kg, 1 eq.), $H^+$ Dowex (10% by weight with respect to compound 1), and methanol, (12.5 vol.). The contents were agitated at gentle reflux (~65° C.) for 19-20 hours, whereupon the reaction was deemed complete by TLC [6:4 ethyl acetate: hexanes (EtOAc:Hex), phosphomolybdic acid (PMA) stain] as well as HPLC analysis. Upon cooling to −25° C., the contents were filtered and the filter washed with 2 volumes of methanol (MeOH). The filtrates were concentrated until rate had significantly decreased. Next, to remove residual methanol, the concentrate was re-dissolved with DCM (4 vol.) and concentrated until distillate rate had significantly decreased. The DCM solvent exchange/concentrated was repeated. After diluting the concentrate with 10 vol. of DCM, 21% sodium carbonate (2 vol.) was added and the contents were agitated for 45 min. The organic layer was separated and recharged to the reactor and extracted with saturated sodium chloride (brine). Following phase cut, the organic solution was dried over sodium sulfate, filtered and recharged to the reactor. Following concentration, and until distillate rate had significantly decreased, the concentrate was solvent exchanged with anhydrous tetrahydrofuran (THF) (2 vol.) and concentrated until the distillate rate had significantly decreased. The solvent exchange was repeated 3-4 times, or until concentrate sample IPC revealed ≤500 ppm MeOH and ≤1250 ppm DCM. The concentrate was diluted with ~2 vol. of anhydrous THF and dropped to a drum, weighed and the wt. % was determined to calculate equivalents for step 2.

Step 2. Synthesis of Compound 3

(3)

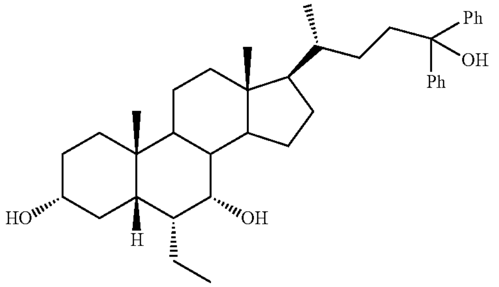

To reaction vessel #1 was charged compound 2 in THF from the previous step. Taking into account the wt. %, the solution was diluted with anhydrous THF to obtain a total anhydrous THF of ~17 volumes. To reactor #2, phenylmagnesium bromide (1.0 M in THF) (5 eq.) was charged and the lines rinsed with minimum ~1 vol. of anhydrous THF. The contents of reaction vessel #1 (i.e. substrate) were slowly charged to the Grignard solution in #2, at such a rate allowing exotherm to occur and slowly ramping reactor temperature towards ~60° C., while maintaining the temperature <65° C. Upon addition completion (and minimal anh. THF line rinse), the reaction mixture was allowed to stir for 1 h, whereupon deemed complete by TLC (6:4 EtOAc: Hex, PMA stain, as well as HPLC analysis. To reaction vessel #3 was charged ~12.5 vol. of a 3N HCl solution and cooled to 2-5° C. The reaction mixture from #2 was slowly reverse quenched into the HCl solution in #3, at such a rate maintaining internal temperature ≤15° C. The quenched reaction mixture was allowed to continue stirring for 45 min at −15° C. Agitation was stopped and the layers were allowed to separate, and phase cut. To the aqueous phase was charged ~10 vol. of methyl t-butylether (MTBE) and the mixture was allowed to vigorously agitate for ~20 min. Following stopping agitation, the phases were separated and the aqueous phase was again extracted with MTBE (~7.5 vol.). The organic phases were combined and extracted with brine (~7.5 vol.), phases cut, and the organic phase dried over sodium sulfate. The filtered solution was concentrated until rate of distillated had significantly reduced. Absolute ethanol (4 vol.) was added and concentrated until rate of distillated had significantly reduced. The ethanol solvent exchange was repeated and the concentrate was diluted with ~4 vol. of absolute ethanol and dropped to a drum, weighed and wt. % determined to calculate equivalents for step 3.

Step 3. Synthesis of Compound 3A (3A)

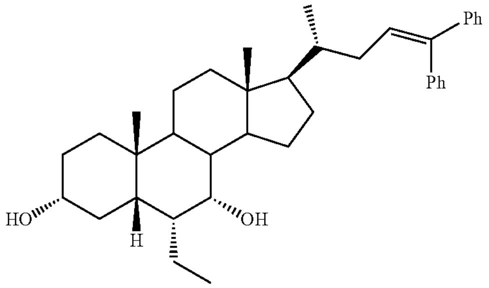

To a reaction vessel was charged Compound 3 in absolute ethanol from the previous step. Taking into account the wt. %, the solution was diluted with absolute ethanol to obtain a total amount of absolute ethanol equaling 9-10 volumes. p-Toluenesulfonic acid (0.05 eq) was added and the reaction was heated to 75° C. for 16 h. Reaction completion was determined by TLC (4:6 EtOAc:Hex, PMA stain) as well as by HPLC analysis. After cooling the contents to <20° C., sat. aq. sodium bicarbonate (0.1 eq.) was charged. The reaction mixture was concentrated to ~¼th of its original volume and was diluted with DCM (7 vol.). Next, sat. aq. sodium bicarbonate (7 vol.) was added and the mixture was vigorously agitated, phases allowed to separate, and phase cut. To the organic layer was charged brine (3 vol.). The mixture was vigorously agitated, phases allowed to separate, and phase cut. The organic layer was dried over sodium sulfate, filtered, and concentrated until rate of distillated had significantly reduced. Anhydrous THF (4 vol.) was added and the diluted solution concentrated until rate of distillated had significantly reduced. The anhydrous THF solvent exchange/concentration was repeated. The concentrate was diluted in anhydrous THF (4 vol.), dropped to a drum, weighed and the wt. % determined to calculate equivalents for step 4.

Step 4. Synthesis of Compound 4

(4)

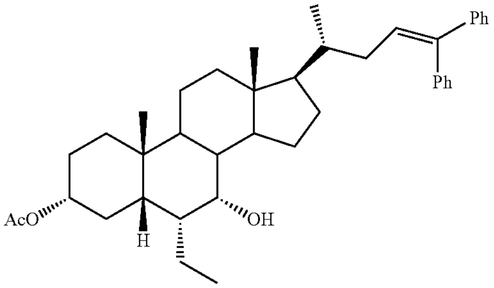

To a reaction vessel was charged Compound 3A in anhydrous THF from the previous step. Taking into account the wt. %, the solution was diluted with additional THF to obtain a total amount of THF equaling ~6 volumes. Pyridine (1.66 eq.) and acetic anhydride (1.66 eq.) were added. Dimethylaminopyridine (DMAP) (0.07 eq.) was dissolved in 10 vol. THF (with respect to DMAP) in a separate vessel and slowly charged to the reaction mixture, while maintaining reaction temperature ≤30° C. The reaction was held at 25° C. for 16 h. Reaction completion was determined by TLC (4:6 EtOAc:Hex, PMA stain) as well as by HPLC analysis. Upon completion, the reaction was cooled to 0-5° C. and slowly quenched with water (2 vol.), while maintaining a quench temperature ≤25° C. Agitation was stopped and the layers allowed to separate. Following phase cut, the aqueous layer was extracted two times with DCM (2 vol. and 1 vol., respectively), and the combined organic layers were extracted in sequence with 1N HCl (4 vol.), 9% aq. sodium bicarbonate (2 vol.), and brine (2 vol.). The organic layer was dried over sodium sulfate, filtered, and concentrated to dryness.

Step 5A. Synthesis of Compound 5

(5)

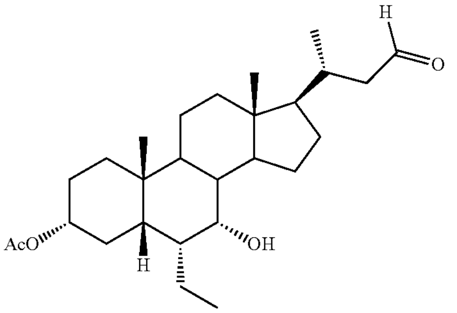 [SMILES: CC[C@H]1[C@@H](O)C2C3CC[C@H]([C@H](C)CC=O)[C@@]3(C)CCC2[C@@]2(C)CC[C@@H](OC(C)=O)C[C@@H]12]

To a reaction vessel was charged Compound 4 with the aid of DCM (5.7 vol.) and methanol (1.5 vol.). Upon agitating and attaining homogeneity, the reaction mixture was cooled to −65 to −70° C. Ozone (via an ozone generator) was bubbled through the solution, while maintaining temperature ≤−60° C., until solution turns greenish/blue. Reaction completion is confirmed by quenching a small aliquot with triphenylphosphine (TPP) and analyzing by TLC (2:8, EtOAc:Hex) and HPLC. The resulting intermediate ozonide was very slowly quenched with a solution of triphenylphosphine (1.12 eq.) pre-dissolved in DCM (0.7 vol. with respect to substrate) maintaining a quench temperature ≤−50° C. during addition. The reaction mixture was allowed to slowly warm (over ~6 h) to 0±5° C. Water (4.8 vol.) was slowly added while maintaining internal temperature <5° C. The mixture was transferred to a separatory vessel and the organic layer was separated. The aqueous layer was back-extracted with DCM (2 vol.), phase cut and the combined organic layers were washed with brine (1.1 vol.), phase cut and dried over sodium sulfate before being concentrated in vacuo to dryness.

Steps 5B and 5C. Synthesis of Compound 6

(6)

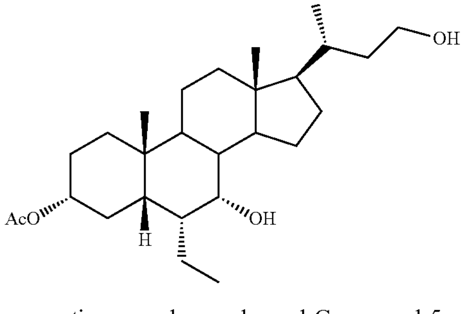

To a reaction vessel was charged Compound 5 with the aid of 200 proof ethanol (2 vol.). Upon agitating and attaining homogeneity, the reaction mixture was cooled to 0±5° C. To the mixture was charged portion-wise sodium borohydride (2.2 eq.) at such a rate as to maintain reaction temperature ≤5° C. After allowing the reaction to warm to 15±5° C., the reaction was determined complete analyzing by TLC (4:6, EtOAc:Hex) and HPLC. After cooling the reaction mixture to 0±5° C., the reaction was quenched by adding 1N HCl (~4.5-5 vol.) dropwise (monitoring pH towards end of the quench; desired pH=2), while maintaining a temperature ≤5° C. The contents were transferred to a separatory vessel and DCM (2.7 vol.) was added. The organic layer was separated and the aqueous layer was back-extracted with DCM (2 vol.) and phase cut; the combined organic layers were washed with brine (1.3 vol.), phase cut and dried over sodium sulfate before being concentrated in vacuo to dryness. The residue was purified by column chromatography by gradient eluting with EtOAc and Hex and concentration of pure fractions to provide pure compound 6 (in about 70% overall yield).

Step 6. Synthesis of Compound 7A (7A)

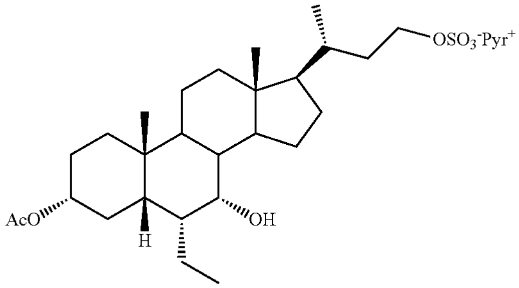

To a reaction vessel was charged Compound 6 (250.8 g, 1 eq.) with the aid of DCM (5.5 vol.). Upon agitating and attaining homogeneity, sulfur trioxide pyridine complex (1.05 eq.) was charged in one shot. The reaction mixture was agitated at room temperature for 1 h and was determined complete analyzing by HPLC. The reaction contents were transferred to a rotary evaporator (rotovap) and concentrated to near dryness. Following adding methanol (MeOH) (0.4 vol.), the resulting solution was concentrated to dryness. The foam solid was re-diluted with MeOH (0.4 vol.) and eluted through a silica plug (~8/1 wt./wt. % with respect to Compound 6) with MeOH. All fractions containing product determined by TLC, (9:1, DCM:MeOH) were concentrated in vacuo to dryness and purified via silica gel column to afford 329.8 g of pure Compound 7A, in 93% yield; 98% pure.

Step 6B. Synthesis of Compound 7B (7B)

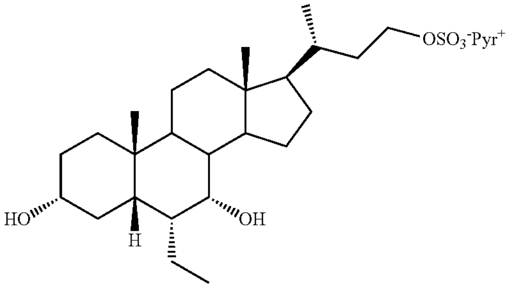

To a reaction vessel was charged compound 7A with the aid of anhydrous, denatured EtOH (11.9 vol.). After adding water (2.8 volume equivalent) and Amberlyst H+ resin (0.5 wt./wt. % with respect to compound 7A), the reaction mixture was agitated at 40±5° C. for 60-70 h. The reaction was determined complete by HPLC analysis. The reaction contents were cooled to room temperature, filtered (to remove resin), transferred to a rotary evaporator and concentrated to near dryness.

Removal of residual acetic acid: To each rotovap flask was charged water (~3.2/1, wt./wt. % water/mass of contents of flask). The contents were concentrated to near dryness. The operation was repeated by charging the same amount of water as charged previously and concentrating to dryness. The residual acetic acid was determined by $^{1}H$ NMR relative integration, wt./wt. %.

Step 6C. Synthesis of Compound 7C (7C)

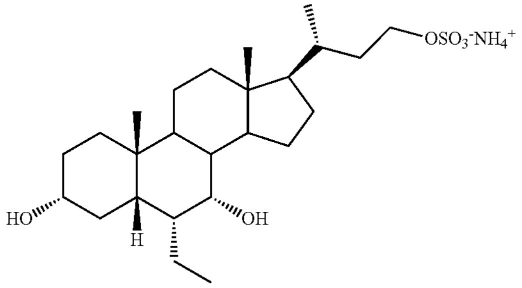

Following charging to each rotovap flask water (the same amount as charged previously to each flask), each flask was charged with 28% ammonium hydroxide until pH=10. The contents of each rotovap flasks were concentrated to near dryness. Again, the same amount of water was charged to each flask as well as 28% ammonium hydroxide until pH=10. Following concentration to dryness (or until minimal amount of water distillate was observed), a sample of each rotovap flask employed was submitted for residual pyridine (GC).

Step C. Synthesis of Compound 7

(7)

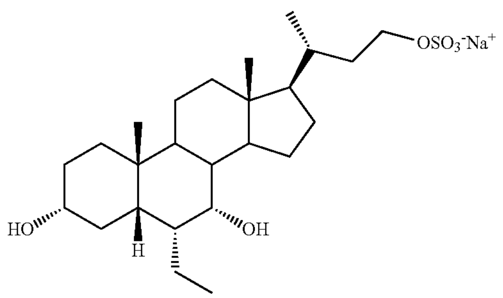

To a separatory vessel was charged compound 7C with the aid of water (6.4 vol.). After adding a 4/1 by volume mixture of MTBE/2-Methyltetrahydrofuran (4.9 vol. total) and agitating for 1 min, the phases were separated. To the aqueous phase was added MTBE (2.5 vol.) and the mixture was agitated for 1 min before phase cut. The aqueous phase was concentrated via rotary evaporator, diluted with water (~3-4 vol. for each flask involved) and re-concentrated. The water solvent exchange/concentration was repeated and the residue was re-dissolved in water (~3 vol.) and passed slowly through an ion exchange column (DIAION™ resin Na+ form, 8.1/1, wt./wt. resin/compound 7C). Fractions containing color (brown to light tan) were concentrated to dryness (or near dryness) and diluted with water (4.35 vol.) and lyophilized. After lyophilizer cycle complete (and KF≤5%), the resulting fluffy solid was added to reaction vessel containing absolute ethanol (3.8-4.0 vol.) until light slurry observed. The solution was polish filtered to remove any trace sodium sulfate by-product. Following concentration to dryness, the residue was diluted with water (4 vol.) and concentrated to dryness (residual EtOH removal). After dilution of the residue with water (4.35 vol.), the solution was re-subjected to lyophilization. The molecular weight of the anion of Compound 7 ($C_{25}H_{43}O_6S$) was confirmed by high-resolution electrospray ionization mass spectroscopy as 471.28 m/e. The process afforded 316.1.g of Compound 7, 99% pure by HPLC (ELSD). Other batches of Compound 7 prepared by the same process afforded Compound 7 in about 72% yield and purity of 99.2% by HPLC.

Compound 7 was also further purified by reverse phase chromatography. The procedure entailed dissolving Compound 7 in WFI (10.1 vol.) and loaded on radial compressed Biotage Flash 400L reverse phase column apparatus. Gradient of HPLC grade acetonitrile (ACN) ratio to WFI was slowly increased and fractions were analyzed by HPLC to determine desired pure fractions (>90 to 100% pure). Pure fractions were then concentrated to reasonable volume to load into lyophilizer. (HPLC Assay as is (wt/wt %) was 103.5%).

The invention claimed is:

1. A method of preparing a sodium salt of a compound of formula (A)

(A)

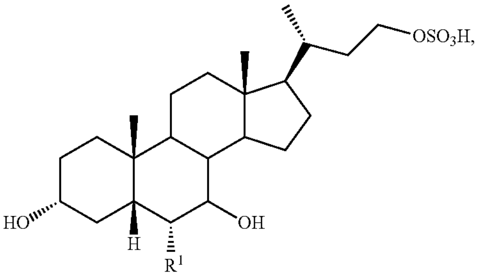

wherein $R^1$ is H or $C_1$-$C_6$ alkyl, the method comprising the steps of:

(a) dissolving an ammonium salt of the compound of formula (A) in an aqueous solution; and (b) passing the aqueous solution through a cation-exchange resin, wherein the cation-exchange resin is $Na^+$ form wherein the compound of formula (A) is prepared through the steps of converting the aldehyde of a compound of formula (B) with a reducing agent to prepare a compound of formula (C)

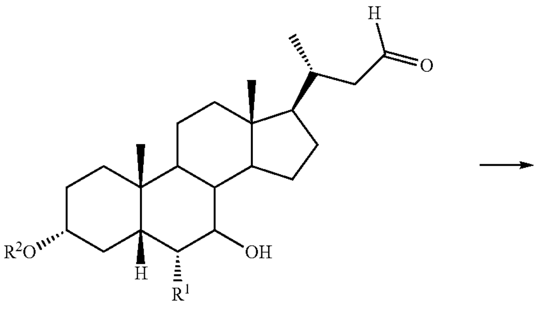

(B)

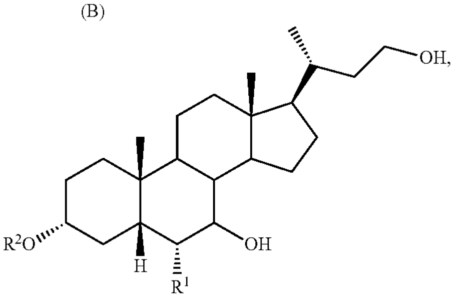

(C)

wherein $R^2$ is a protecting group;

converting the compound of formula (C) with a sulfating reagent to prepare a compound of formula (D)

(D)

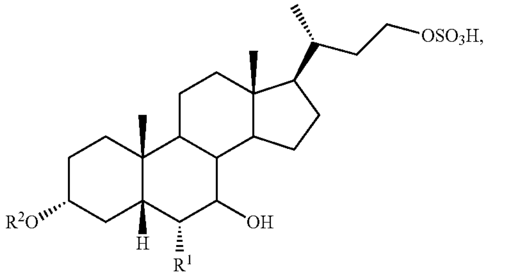

or a pharmaceutically acceptable salt thereof; and deprotecting the C-3 hydroxyl of the compound of formula (D) to form a compound of formula (A).

2. The method of claim 1, further comprising lyophilization of the sodium salt of the compound of formula (A).

3. The method of claim 2, further comprising purifying the sodium salt of the compound of formula (A) by reverse phase chromatography.

4. The method of claim 1, wherein $R^1$ is $C_1$-$C_4$ alkyl, and the C-7 hydroxyl is in the alpha-orientation.

5. The method of claim 1, wherein $R^2$ is —C(O)$C_1$-$C_4$ alkyl.

6. The method of claim 1, wherein the reducing reagent in step (a) is selected from $NaBH_4$, $NaCNBH_3$, $LiBH_4$, $(i\text{-}Bu_2AlH)_2$, and an organoborane.

7. The method of claim 1, wherein the sulfating reagent in step (b) is selected from sulfur trioxide pyridine, sulfur trioxide trimethylamine, sulfur trioxide triethylamine, sulfur trioxide N,N-dimethylformamide, poly(4-vinylpyridine) sulfur trioxide, chlorosulfonic acid, oleum, and sulfamic acid.

8. The method of claim 1, wherein $R^2$ is acetyl and the deprotection in step (c) is performed under acidic conditions.

9. The method of claim 1, further comprising converting a compound of formula (E) to prepare the compound of formula (B):

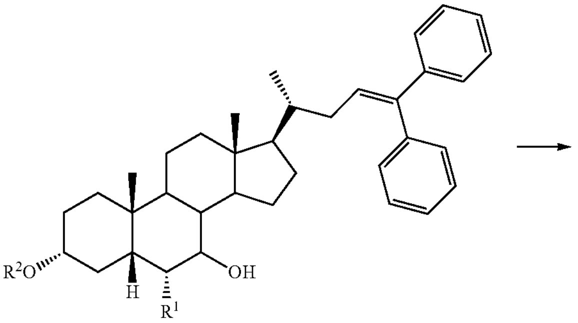

(E)

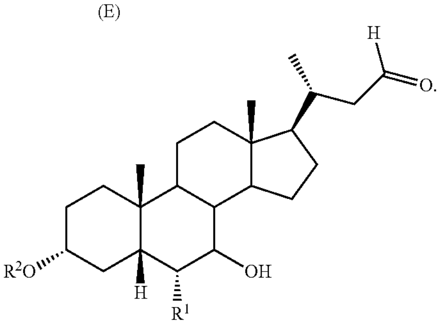

(B)

10. The method of claim 9, further comprising protecting the C-3 hydroxyl of a compound of formula (F) to prepare the compound of formula (E):

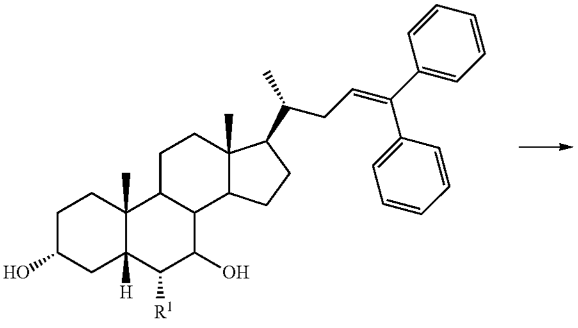

(F)

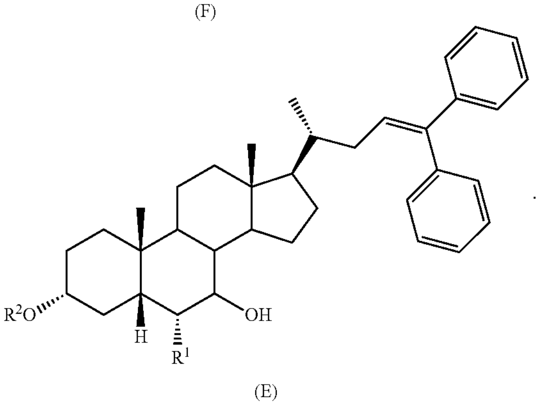

(E)

11. The method of claim 10, further comprising converting a compound of formula (G) to prepare the compound of formula (F):

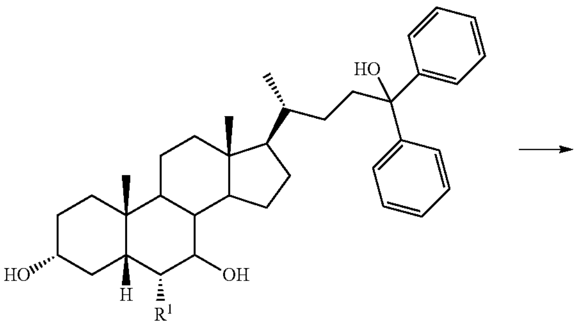

(G)

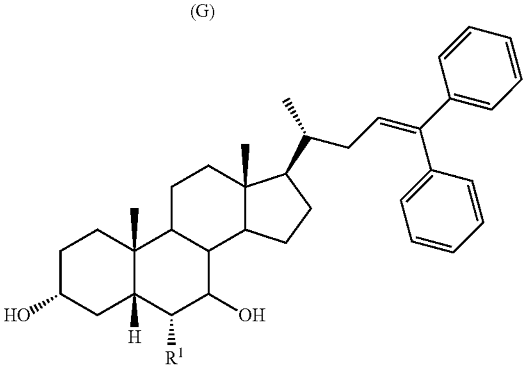

.

(F)

12. The method of claim 11, further comprising converting a compound of formula (H) to prepare the compound of formula (G):

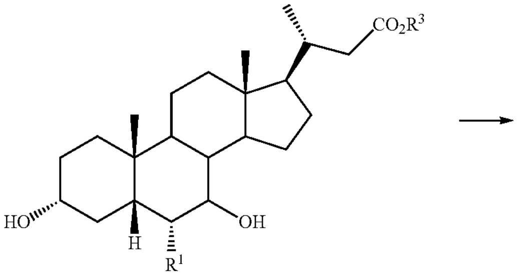

(H)

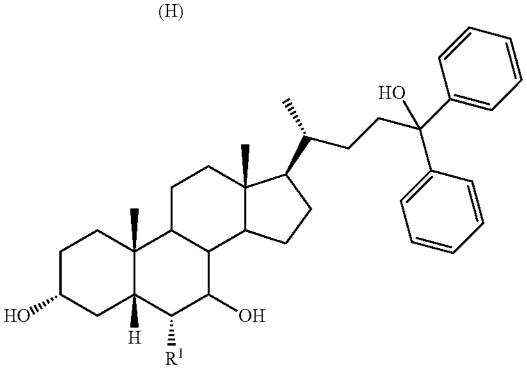

, (G)

wherein $R^3$ is $C_1$-$C_6$ alkyl.

13. The method of claim 12, further comprising converting a compound of formula (I) to afford the compound of formula (H):

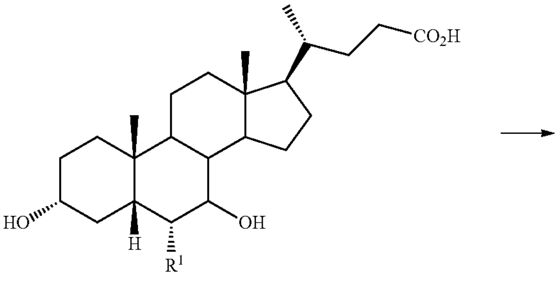

(I)

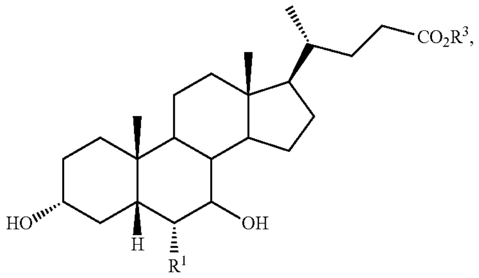

(H)

wherein $R^3$ is $C_1$-$C_6$ alkyl.

14. The method of claim 1, wherein the compound of formula (A) is compound 7, (7)

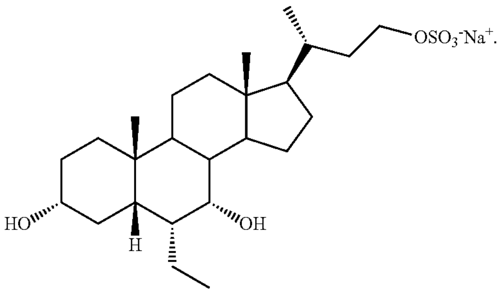

wherein the method further comprises converting compound 7B to compound 7C:

(7B)

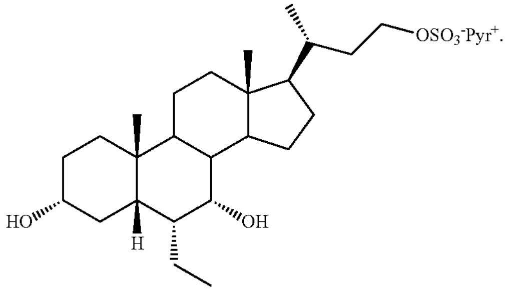

(7C)
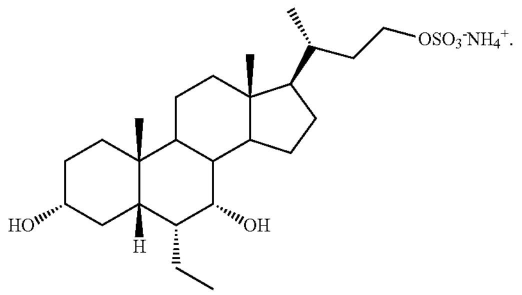
and
further converting compound 7C to compound 7.
* * * * *